US00PP20214P2

(12) United States Plant Patent
Horvath

(10) Patent No.: US PP20,214 P2
(45) Date of Patent: Aug. 11, 2009

(54) ***POLEMONIUM* PLANT NAMED 'HEAVEN SCENT'**

(50) Latin Name: *Polemonium*
Varietal Denomination: Heaven Scent

(76) Inventor: Brent Horvath, 10702 Seaman Rd., Hebron, IL (US) 60034

( * ) Notice: Subject to any disclaimer, the term of this patent is extended or adjusted under 35 U.S.C. 154(b) by 0 days.

(21) Appl. No.: 12/011,718

(22) Filed: Jan. 30, 2008

(51) Int. Cl.
*A01H 5/00* (2006.01)

(52) U.S. Cl. ..... Plt./470

(58) Field of Classification Search ..... Plt./470
See application file for complete search history.

*Primary Examiner*—Annette H Para

(57) ABSTRACT

A new, distinct *Polemonium* plant as shown and described, characterized by red new growth to the foliage in spring, grape scented flowers and a medium height.

2 Drawing Sheets

Latin name: *Polemonium.*
Cultivar name: 'Heaven Scent'.

BACKGROUND OF THE INVENTION

The present invention relates to a new and distinct hybrid of *Polemonium* plant named 'Heaven Scent' characterized by red new growth in the foliage in spring, grape scented flowers and a medium height compared to the parents. The new *Polemonium* was raised as a seedling from a controlled cross of *Polemonium* reptans, not patented, and *Polemonium* yezoense 'Purple Rain', not patented, in Hebron, Ill. in 2004. The selection of the new plant was due to its' red new growth in the foliage, grape scented flowers and a medium height compared to the parents. Sterile, asexual division, and tissue culture have been the means of reproduction. Division propagation has taken place at a nursery Hebron, Ill. since 2005. The new *Polemonium* has shown to be stable and identical in reproduction to the parent after dividing over 60 plants resulting in over 700 divisions from 2005 to 2007. The plant is also being tissue cultured at a nursery in Zeeland, Mich. where over 5,000 plants have been grown out.

SUMMARY OF THE INVENTION

In the following description, color references are made to the Royal Horticultural Society Colour Chart. The new *Polemonium* plant named 'Heaven Scent' characterized by red new growth in the foliage in spring, grape scented flowers and a medium height compared to the parents have been observed to be unique and stable.

Plants of the new *Polemonium* can be compared to plants of the male or pollen parent *Polemonium* reptans. 1. The new plant is a hybrid and does not produce seed while the species is fertile and produces seed. 2. The new *Polemonium* has red new growth RHS color 200A while the species foliage is green. 3. The new *Polemonium* flower color is RHS 94B while *Polemonium* reptans has a blue flower color. 4. The new *Polemonium* has grape scented flowers while *Polemonium* reptans does not. 5. The new *Polemonium* has a mature height of 42–55 cm while the parent *Polemonium* reptans has a mature height of 30–35 cm.

Plants of the new *Polemonium* can also be compared to the other parent plant *Polemonium* yezoense 'Purple Rain'. 1. The new plant is a hybrid and does not produce seed while the other parent plant *Polemonium* yezoense 'Purple Rain' is fertile and produces seed. 2. The new *Polemonium* has a mature height of 42–55 cm while the parent *Polemonium* yezoense 'Purple Rain' has a mature height of 65 cm.

DESCRIPTION OF PHOTOGRAPHS

Figure 1:
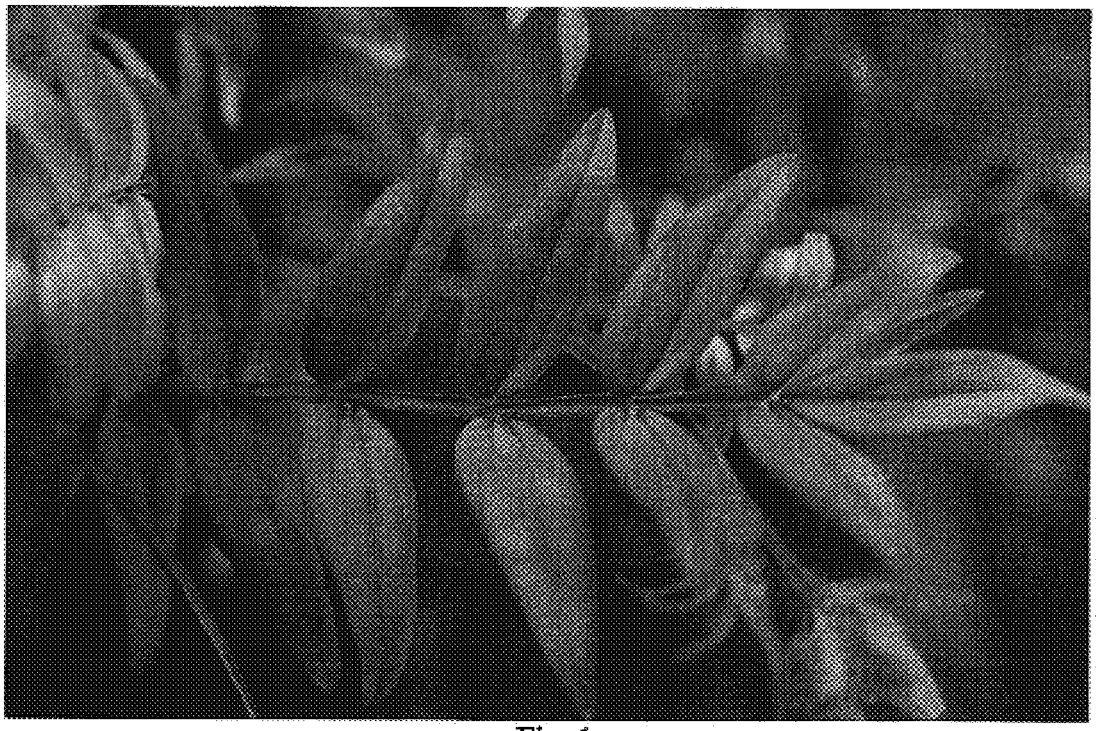

FIG. 1. Close up of the foliage.

Figure 2:
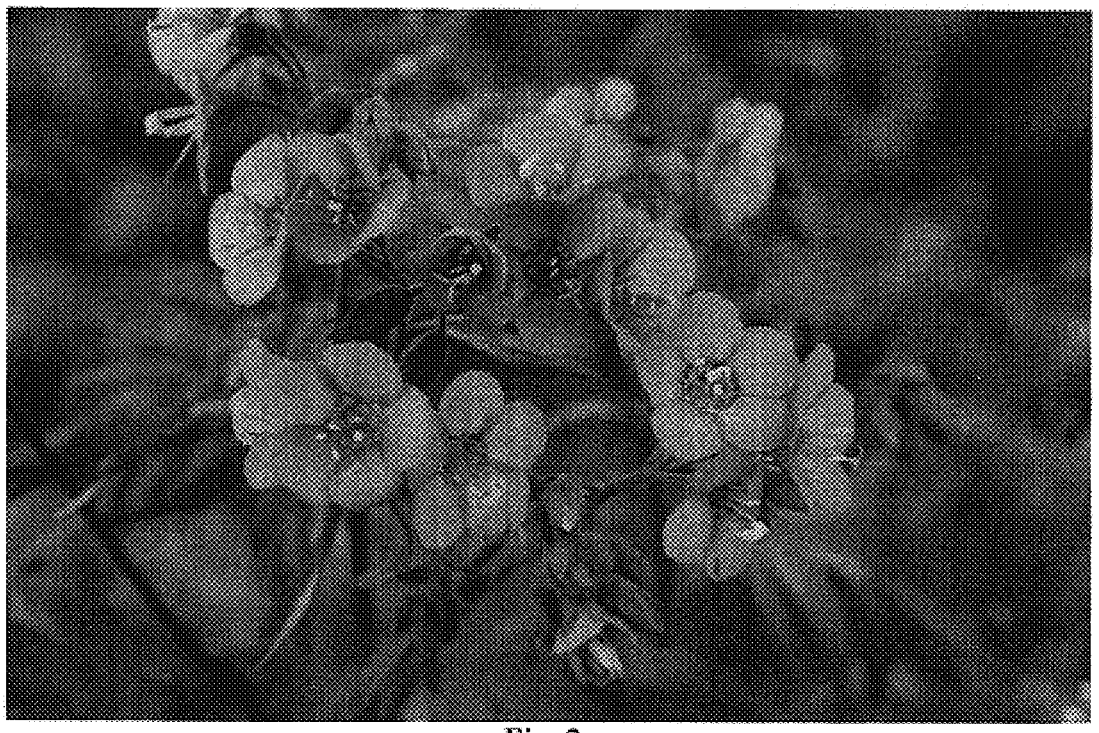

FIG. 2. Close up of the flower.

Figure 3:
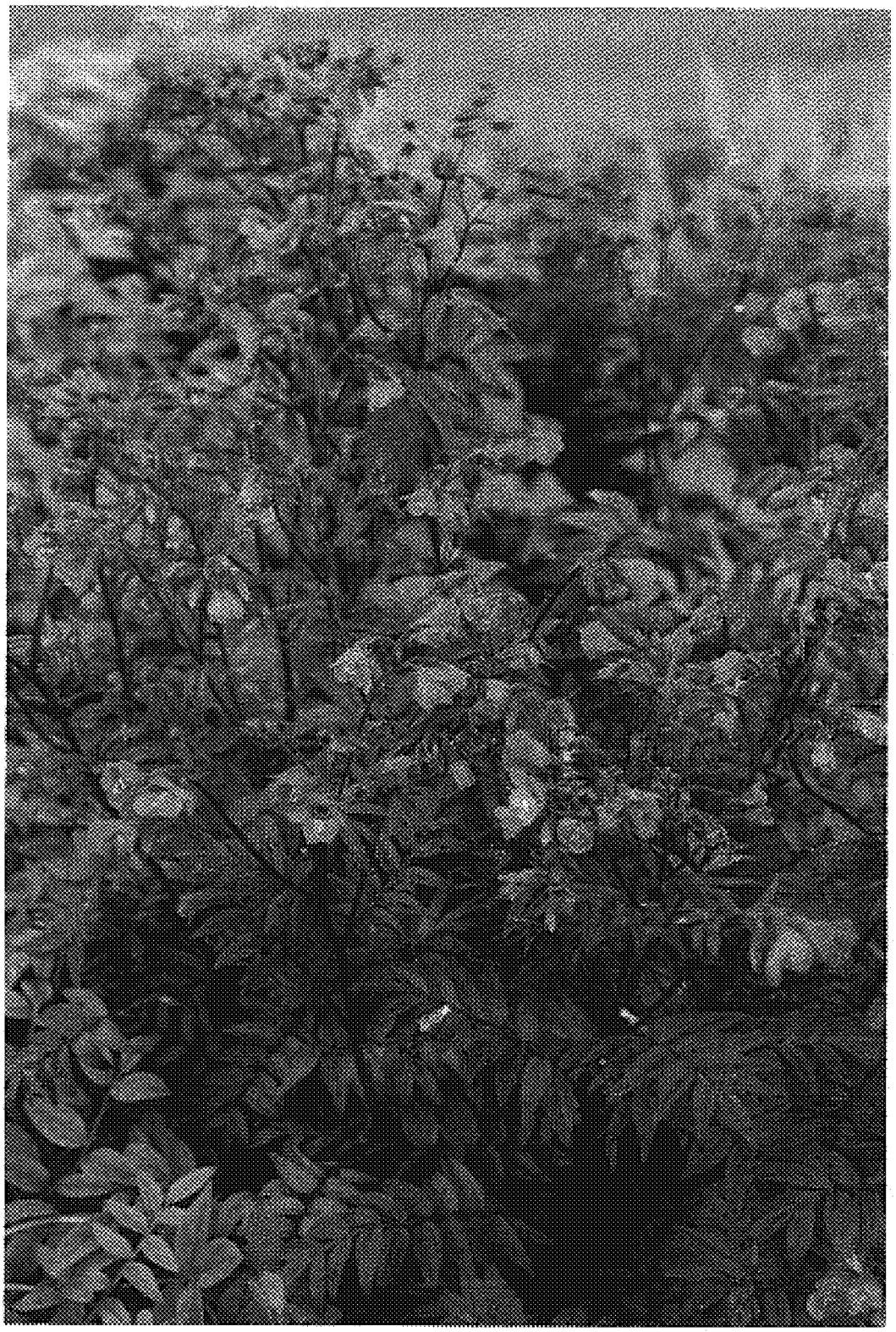

FIG. 3. Blooming plant in May.

DETAILED BOTANICAL DESCRIPTION

In the following description, color references are made to The Royal Horticultural Society Colour Chart. Plants used for the description were grown for two seasons.

Botanical classification: *Polemonium hybrida* cultivar Heaven Scent.

Parentage: Male or pollen *Polemonium* reptans and female or seed *Polemonium* yezoense 'Purple Rain'.

Propagation: Vegetative division and tissue culture.

Plant description: Overall habit of the new *Polemonium* is basal clumps starting with red new growth in spring, upright stems topped by purple flowers RHS color 94B in May.

*Plant height.*—42–55 cm.
*Plant width.*—45 cm as a mean.
*Stem diameter.*—3–5 mm.

Foliage:

*Type.*—Deciduous.
*Shape.*—Pinnate.
*Arrangement.*—Opposite compound.
*Petiole.*—2 cm long and 5 mm wide.
*Length.*—12 cm.
*Width.*—7 cm.
*Leaflet length.*—30–35 mm.
*Leaflet width.*—1 cm.
*Leaflet shape.*—Lanceolate.
*Adaxial leaf description.*—New growth color is 200 A. The mature green foliage is color 147 A.
*Abaxial leaf description.*—The mature green foliage is color 138 B.

Flower:

*Flower type.*—Panicle on basal flowering stems.
*Flower color.*—94 B.
*Flower diameter.*—2 cm across.
*Flower number.*—Approximately 25–40 per raceme or panicle.
*Flowering stems.*—Up to 55 cm stems.
*Bloom period and duration.*—Late April into May and sporadically into June.
*Scent.*—Grape scented.
*Petal count.*—5.
*Petal margin.*—Entire.
*Petal base.*—Fused.
*Petal arrangement.*—Imbricate.
*Petal apex.*—Rounded.
*Petal venation.*—Close to 72 A.
*Inflorescence diameter.*—About 10 mm.
*Carpel color.*—None, sterile.
*Sepal size.*—8 mm long, 3–5 mm diameter across.
*Sepal color.*—N77.
*Peduncle color.*—N77.
*Flower number.*—600.
*Fertility.*—Sterile, no anthers, 5 stamens.
*Fruit.*—None.
*Disease resistance.*—Resistance to diseases common to *Polemonium* has not been observed on plants grown under nursery conditions.

I claim:

1. A new, distinct *Polemonium* plant as shown and described, characterized by red new growth to the foliage in spring, grape scented flowers and a medium height.

* * * * *